(12) United States Patent
Buchnik et al.

(10) Patent No.: US 12,064,250 B2
(45) Date of Patent: Aug. 20, 2024

(54) GENERIC BOX FOR ELECTROPHYSIOLOGY SYSTEM ADAPTERS

(71) Applicant: Biosense Webster (Israel) Ltd., Yokneam (IL)

(72) Inventors: Yael Buchnik, Adi (IL); Vadim Gliner, Haifa (IL); Uriel Hod, Ein Ayala (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 774 days.

(21) Appl. No.: 17/135,253

(22) Filed: Dec. 28, 2020

(65) Prior Publication Data

US 2022/0202468 A1  Jun. 30, 2022

(51) Int. Cl.
*A61B 5/24* (2021.01)
*A61B 5/30* (2021.01)
(Continued)

(52) U.S. Cl.
CPC .................. *A61B 5/24* (2021.01); *A61B 5/30* (2021.01); *A61B 2018/00095* (2013.01);
(Continued)

(58) Field of Classification Search
CPC .. A61B 5/24; A61B 5/30; A61B 18/14; A61B 2018/00095; A61B 2018/00172;
(Continued)

(56) References Cited

U.S. PATENT DOCUMENTS 4,929,874 A * 5/1990 Mizuno ................. G01M 7/022
318/128
5,391,199 A   2/1995 Ben-Haim
(Continued)

FOREIGN PATENT DOCUMENTS

EP    3451540 A1   3/2019
WO   1996005768 A1  2/1996

OTHER PUBLICATIONS

Extended European Search Report dated May 31, 2022, from corresponding European Application No. 21217670.5.

*Primary Examiner* — Catherine M Voorhees
(74) *Attorney, Agent, or Firm* — Troutman Pepper Hamilton Sanders LLP

(57) ABSTRACT

Apparatus, including an enclosure having a base and a cover with respective conductive layers. The conductive layers connect to form a shield attenuating electromagnetic radiation originating outside the enclosure in a range of 10 kHz-100 kHz by at least 20 dB within the enclosure. An adapter circuit within the enclosure processes electrophysiological signals to generate an output signal. A first connector passing through the enclosure connects to a probe to receive the electrophysiological signals and convey them to the adapter circuit. A second connector passing through the enclosure receives the output signal from the adapter circuit and conveys it to a console. A control input receives a control signal indicative of a frequency within the range, and a sensing circuit senses a magnetic field within the enclosure and outputs a warning signal when the magnetic field at the frequency indicated by the control signal exceeds a preset threshold.

16 Claims, 4 Drawing Sheets

(51) Int. Cl.
  *A61B 18/00* (2006.01)
  *A61B 18/14* (2006.01)
(52) U.S. Cl.
  CPC ............... *A61B 2018/00172* (2013.01); *A61B 2018/00178* (2013.01); *A61B 2018/00898* (2013.01); *A61B 18/14* (2013.01); *A61B 2562/0223* (2013.01); *A61B 2562/18* (2013.01); *A61B 2562/182* (2013.01); *A61B 2562/225* (2013.01)
(58) Field of Classification Search
  CPC ........... A61B 2018/00178; A61B 2018/00898; A61B 2562/0223; A61B 2562/18; A61B 2562/182; A61B 2562/225; A61B 5/062; A61B 2560/0242; A61B 2560/045; A61B 5/308; A61B 5/287; A61B 18/12; A61B 2018/0702; A61B 2018/00077; A61B 2018/00636; A61B 2018/00994; A61B 2018/0256; A61B 18/02
  See application file for complete search history.

(56) References Cited

U.S. PATENT DOCUMENTS

| | | | |
|---|---|---|---|
| 6,239,724 B1 | 5/2001 | Doron et al. | |
| 6,332,089 B1 | 12/2001 | Acker et al. | |
| 6,484,118 B1 | 11/2002 | Govari | |
| 6,618,612 B1 | 9/2003 | Acker et al. | |
| 6,690,963 B2 * | 2/2004 | Ben-Haim | A61N 1/32 606/41 |
| 8,456,182 B2 | 6/2013 | Bar-Tal et al. | |
| 10,411,749 B2 | 9/2019 | Witter et al. | |
| 11,690,207 B2 * | 6/2023 | Ishihara | B32B 15/043 174/388 |
| 2002/0065455 A1 | 5/2002 | Ben-Haim et al. | |
| 2003/0120150 A1 | 6/2003 | Govari | |
| 2004/0068178 A1 | 4/2004 | Govari | |
| 2007/0213779 A1 * | 9/2007 | Toffol | A61N 1/08 607/27 |
| 2009/0034169 A1 | 2/2009 | Richardson et al. | |
| 2013/0012808 A1 * | 1/2013 | Govari | G01R 33/025 439/620.21 |
| 2014/0077612 A1 | 3/2014 | Onuma et al. | |
| 2014/0226268 A1 | 8/2014 | O'Neill et al. | |
| 2018/0172867 A1 * | 6/2018 | Gudmundsson | G01V 3/104 |
| 2018/0242880 A1 * | 8/2018 | Bhushan | G01R 33/0023 |
| 2019/0053737 A1 | 2/2019 | Carter et al. | |
| 2019/0275343 A1 * | 9/2019 | Li | A61N 1/37223 |
| 2021/0161592 A1 | 6/2021 | Altmann et al. | |
| 2021/0197356 A1 * | 7/2021 | Chung | B25F 5/008 |
| 2021/0377377 A1 * | 12/2021 | Scholz | H04B 5/0031 |

\* cited by examiner

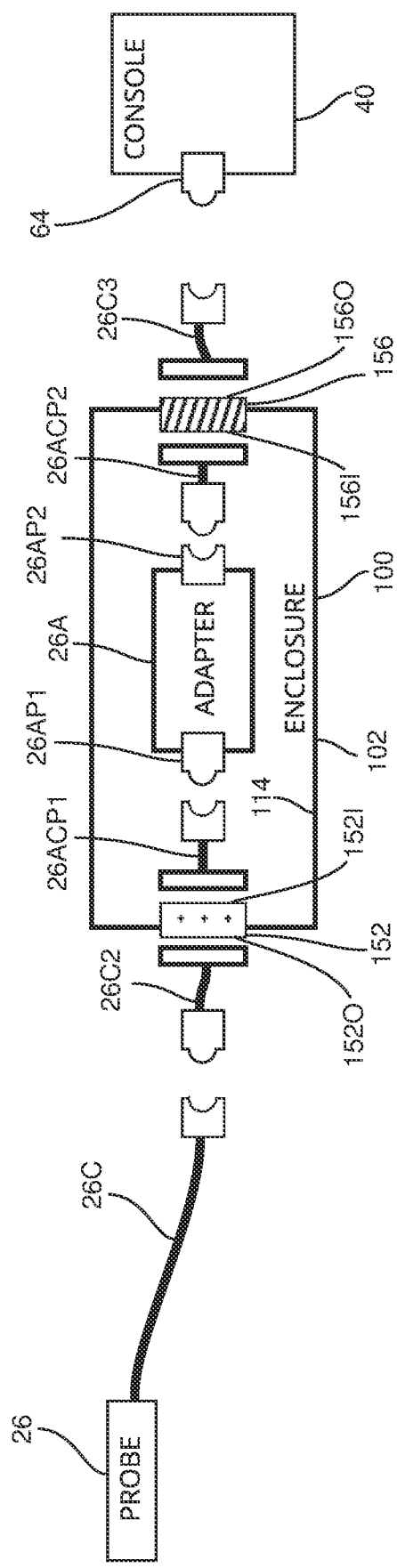
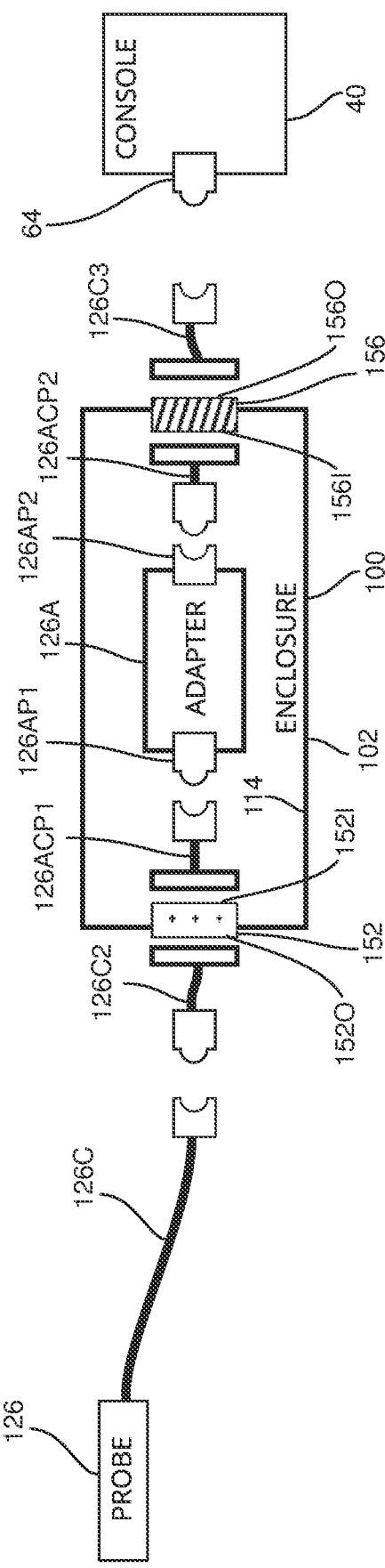

GENERIC BOX FOR ELECTROPHYSIOLOGY SYSTEM ADAPTERS

FIELD OF THE INVENTION

This invention relates generally to an electrophysiological system, and specifically to adapters that change the functionality of the system.

BACKGROUND OF THE INVENTION

Equipment produced for use in medical facilities must comply with multiple standards such as those defining electromagnetic immunity and resistance to transportation vibration. The requirement applies to adapters that add functionality to existing equipment. Such adapters are typically enclosed in dedicated cases. Examples of such cases are referenced below.

U.S. Patent application 2014/0226268, to O'Neill et al., describes cases which are claimed to enclose and/or protect a mobile electronic device from various hazards, such as impact, shock, and/or ingress of potentially damaging substances, such as water, other liquids, dust, dirt, sand, and/or other debris.

U.S. Pat. No. 10,411,749 to Witter, et al., describes a protective enclosure for use with an electronic device. The enclosure is stated to include a cushion layer configured to cover at least a portion of the side surfaces of the electronic device when the electronic device is installed in the protective enclosure.

U.S. Patent application 2009/0034169, to Richardson et al., describes a protective enclosure for an electronic device that has a protective shell that is capable of enclosing and substantially surrounding an electronic device, in a substantially rigid and substantially crush-resistant manner.

SUMMARY OF THE INVENTION

An embodiment of the present invention provides apparatus, including:

an enclosure, consisting of:
a base having a base conductive layer; and
a cover, which has a cover conductive layer and is configured to mate with the base so that the base conductive layer connects to the cover conductive layer so as to form a shield that attenuates electromagnetic radiation originating outside the enclosure in a frequency range of 10 kHz-100 kHz by at least 20 dB within the enclosure; an adapter circuit contained within the enclosure and configured to process electrophysiological signals and generate an output signal in response thereto;

a first connector passing through an outer surface of the enclosure and having a first outer side configured to connect to a medical probe so as to receive the electrophysiological signals therefrom and a first inner side connected to convey the electrophysiological signals to the adapter circuit;

a second connector passing through the outer surface of the enclosure and having a second inner side connected to receive the output signal from the adapter circuit and a second outer side configured to connect to a console so as to convey the output signal thereto;

a control input, configured to receive a control signal indicative of a selection of a frequency within the range; and a sensing circuit, configured to sense a magnetic field within the enclosure and to output a warning signal when the magnetic field at the frequency indicated by the control signal exceeds a preset threshold.

In a disclosed embodiment the apparatus includes a plurality of viscoelastic mounts configured to support the adapter circuit on the base and to attenuate at the adapter circuit mechanical vibrations received by the base.

In another disclosed embodiment the cover mates with a first side of the base, and the apparatus further includes a closed heat dissipator connected to a second side of the base opposite to the first side, the base having vents configured to transfer hot air from a region in proximity to the adapter circuit through the heat dissipator so as to cool the hot air and return cooled air to the region.

In a further disclosed embodiment the apparatus includes a light emitting element formed on the cover, the element being configured to activate in response to generation of the warning signal.

In a yet further disclosed embodiment the sensing circuit includes at least one coil coupled to provide an input signal to a lock-in amplifier. Typically, the medical probe is located in a magnetic field alternating at a preset frequency, and the control signal is indicative of the preset frequency, and is provided to the lock-in amplifier. The preset frequency may be generated by the console, and the lock-in amplifier may receive the control signal from the console via the second connector.

In an alternative embodiment the preset threshold includes a magnetic field having an amplitude of 1 mGauss.

There is further provided, according to an embodiment of the present invention a method, consisting of:

providing an enclosure, including:
a base having a base conductive layer, and
a cover, which has a cover conductive layer and is configured to mate with the base so that the base conductive layer connects to the cover conductive layer so as to form a shield that attenuates electromagnetic radiation originating outside the enclosure in a frequency range of 10 kHz-100 kHz by at least 20 dB within the enclosure;

positioning an adapter circuit within the enclosure, wherein the adapter circuit is configured to process electrophysiological signals and generate an output signal in response thereto;

passing a first connector through an outer surface of the enclosure, the first connector having a first outer side configured to connect to a medical probe so as to receive the electrophysiological signals therefrom and a first inner side connected to convey the electrophysiological signals to the adapter circuit;

passing a second connector through the outer surface of the enclosure, the second connector having a second inner side connected to receive the output signal from the adapter circuit and a second outer side configured to connect to a console so as to convey the output signal thereto;

configuring a control input to receive a control signal indicative of a selection of a frequency within the range; and configuring a sensing circuit to sense a magnetic field within the enclosure and to output a warning signal when the magnetic field at the frequency indicated by the control signal exceeds a preset threshold.

The present disclosure will be more fully understood from the following detailed description of the embodiments thereof, taken together with the drawings, in which:

BRIEF DESCRIPTION OF THE DRAWINGS

FIG. 3A is a schematic block diagram illustrating a probe, an adapter in an enclosure, and a console, and their matching connections, according to an embodiment of the present invention; and FIG. 3B is a schematic block diagram illustrating a probe, an adapter in an enclosure, and a console, and their matching connections, according to an alternative embodiment of the present invention.

DETAILED DESCRIPTION OF EMBODIMENTS

Overview

Over the course of the lifetime of a system configured for use in an electrophysiological procedure, involving insertion of a probe into a human subject, there are typically changes made to both the hardware and the software of the system so as to enhance system functionality. One method for implementing such a change is to insert an adapter, comprising software and/or hardware, between the probe and a controlling console to which the probe is normally connected.

The adapter is typically dedicated to a specific type of probe; for example there may be one adapter for a probe comprising a basket catheter, and another adapter for a probe comprising a lasso catheter (a catheter with a flexible distal end having multiple electrodes).

Embodiments of the present invention provide an enclosure which is configured to house different types of adapters, and which enables each adapter housed to connect to its respective probe, as well as to the controlling console. In addition the enclosure is configured so that each adapter it houses complies with three international standards set by the IEC (International Electrotechnical Commission) including one standard for electromagnetic (EM) radiation shielding. Notwithstanding complying with the EM shielding standard, the enclosure is further configured to measure alternating magnetic field radiation which may traverse a housed adapter, and warn if the level of such radiation is greater than a preset value.

DETAILED DESCRIPTION

Figure 1:
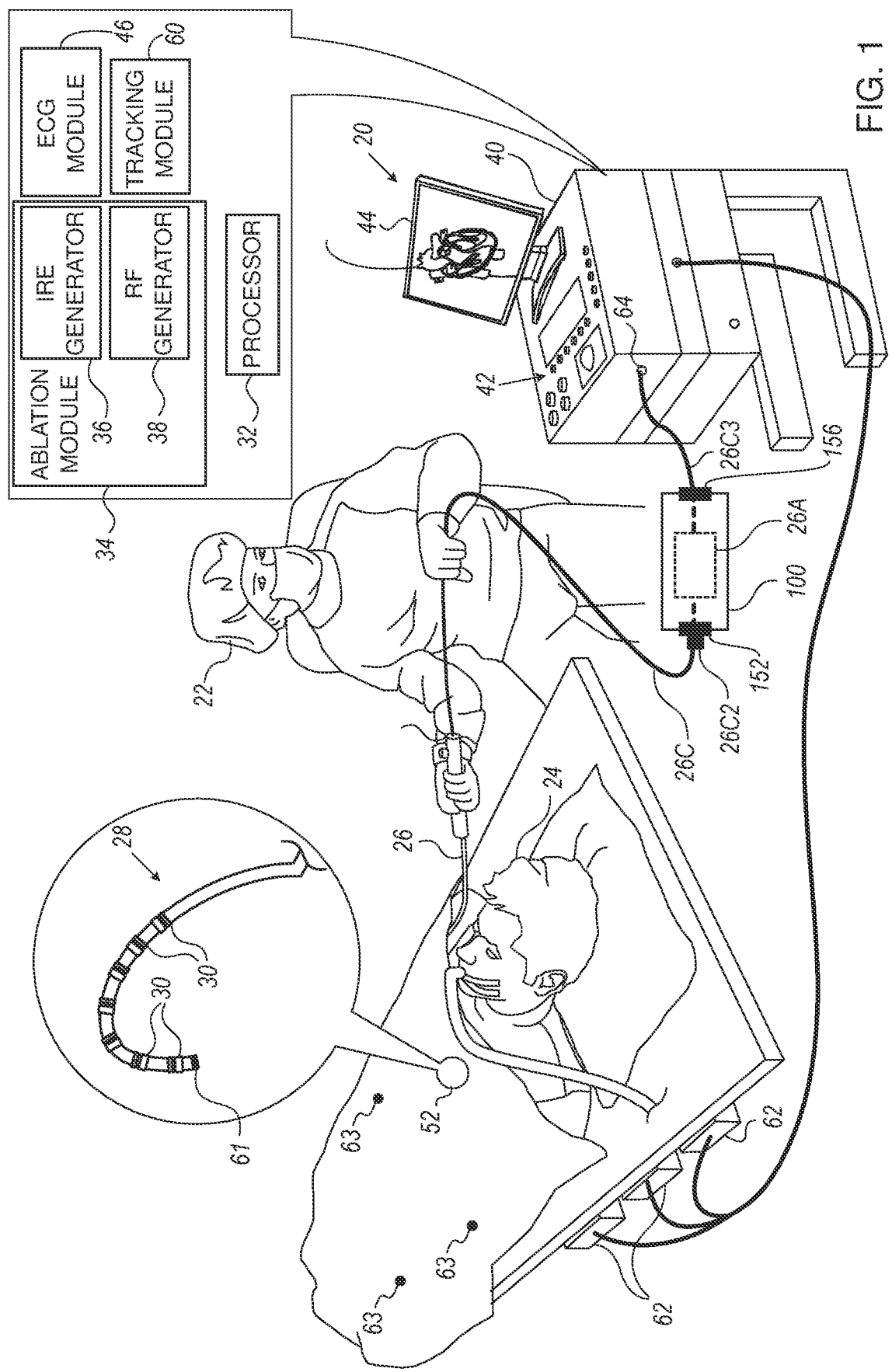
FIG. 1 is a schematic pictorial illustration of an electrophysiological (EP) system used in an EP procedure, according to an embodiment of the present invention.

Reference is now made to FIG. 1, which is a schematic pictorial illustration of an electrophysiological (EP) system 20 used in an EP procedure, according to an embodiment of the present invention. In the pictured embodiment, a physician 22 performs, by way of example, a multi-channel ablation procedure using system 20. Physician 22 performs the procedure on a heart 52 of a subject 24, using a medical catheter probe 26 having a distal end 28 comprising multiple electrodes 30 arranged along the length of the distal end. As well as being configured to perform ablation, electrodes 30 may acquire electrophysiological signals from heart 52, and/or inject electrical signals into the heart. In some embodiments electrodes 30 may also be configured for other functionalities, such as being configured to convey currents to, or receive currents from, external body patches in order to determine, in response to the current magnitudes, a location of the electrodes.

It will be understood that the signals and currents referred to above, to electrodes 30, are transferred through conductive wiring in probe 26. In some embodiments other catheter signals that may not connect to electrodes 30 are also transferred to distal end 28 through conductive wiring in probe 26, for example, signals from a magnetic field sensor 61 at the distal end.

EP system 20 comprises a processor 32 and a number of modules, described below, which can be accessed by the processor to provide functionality to probe 26. Processor 32 and the modules typically reside within a console 40. Console 40 comprises input devices 42, such as a keyboard and a mouse, operated by physician 22. A display screen 44 is located in proximity to console 40. Display screen 44 may optionally comprise a touch screen, thus providing another input device.

Processor 32 typically comprises a programmable processor, which is programmed in software and/or firmware to carry out the functions that are described herein. Alternatively or additionally, the processor may comprise hard-wired and/or programmable hardware logic circuits, which perform at least some of these functions. Although processor 32 and the modules it accesses are shown in the figures, for the sake of simplicity, as separate, monolithic functional blocks, in practice some of these functions may be combined in a single processing and control unit. The modules accessed by the processor are described below.

An ablation module 34 is used by the processor to provide ablation power to electrodes 30. The ablation module in turn comprises an IRE (irreversible electroporation) generator 36 and/or an RF (radiofrequency) generator 38. Cell death following IRE results from apoptosis (programmed cell death) and not necrosis (cell injury, which results in the destruction of a cell through the action of its own enzymes) as in RF ablation.

An IRE generator similar to generator 36 is described in U.S. patent application Ser. No. 16/701,989, which is incorporated herein by reference. IRE generator 36 generates trains of electrical pulses, which are directed to selected electrodes 30 for performing an IRE procedure. The waveforms (timing and amplitude) of the trains of electrical pulses are controlled by processor 32.

RF generator 38 typically generates sinusoidal power of the order of 100 W, at frequencies of the order of hundreds of kHz.

A tracking module 60 is coupled to electromagnetic position sensor 61 in distal end 28 and the module also provides power, at different preset frequencies, typically in the range of approximately 1 kHz to approximately 20 kHz to magnetic-field generators 62. In the presence of an external alternating magnetic field generated by generators 62, the electromagnetic position sensor outputs signals that vary with the position of the sensor. Based on these signals, tracking module 60 may ascertain the positions of electrodes 30 in heart 52.

A method of position tracking using external magnetic fields is implemented in the CARTO™ system, produced by Biosense Webster Inc. (Irvine, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, which disclosures are hereby incorporated by reference.

Alternatively or additionally, module 60 may use a tracking system based on currents transferred through, or impedances seen by, electrodes 30. In such a system module 60 estimates the position of a given electrode 30 in response to currents or impedances between the given electrode and a plurality of surface-electrodes 63 that are coupled to the skin of subject 24. An Advanced Current Location (ACL) system, made by Biosense-Webster (Irvine, California), which is described in U.S. Pat. No. 8,456,182, which disclosure is incorporated herein by reference, is such a tracking system.

An electrocardiogram (ECG) module 46 is used by processor 32 to acquire, process, and analyze cardiac signals generated at electrodes 30. The analysis typically includes measuring parameters such as local activation time (LAT) at the positions of the electrodes. The values of the parameters may be displayed, typically in graphical form, to operator 22 on screen 44. The processor may also use module 46 to inject stimulating signals into selected electrodes 30.

While probe 26 may be directly connected to an interface 64 in console 40 by cabling 26C, in embodiments of the present invention an adapter circuit 26A, herein also termed adapter 26A, housed in an enclosure 100, is connected in series between interface 64 and the cabling. To implement the series connection, cabling 26C is connected, via a cable adapter 26C2, to a connector 152 in enclosure 100, additional cabling 26C3 is connected between a connector 156 in the enclosure and interface 64, and adapter 26A is coupled internally to connectors 152 and 156. The internal connections of adapter 26A within enclosure 100 are described below with reference to FIGS. 2A and 2B.

In the direct connection of probe 26 and cabling 26C, processor 32 uses modules 34, 46, and/or 60 to generate a predetermined functionality for electrodes 30. Connecting adapter 26A, as described herein, adds additional functionality to the predetermined functionality. Typically the additional functionality is introduced into system 20 when a version of the software and hardware of the system is updated.

An example of additional functionality is an updated method for calculating values of LAT. The additional functionality may be implemented in the adapter in software, but adding the functionality using hardware, or with a mixture of hardware and software, may enhance the flexibility and/or the speed of the added functionality.

Other examples of additional functionality include:

adding the potential of operating new intra-cardiac-ECG channels for a legacy system;

adding a real-time display of a catheter tip surface, as well as temperature and microelectrode signals, in a legacy System; and providing new signal conditioning properties (such as changed amplification and filtering) together with a memory for storing calibration parameters of probe 26.

As stated above, connecting adapter 26A adds additional functionality, and the adapter may be connected between interface 64 and cabling 26C without housing the adapter in enclosure 100. However, enclosure 100 is configured so that in addition to enclosing the adapter in the enclosure the enclosure enables the adapter to comply with the following standards of the International Electrotechnical Commission (IEC) of Geneva, Switzerland: IEC 60601-1-2 for electromagnetic shielding; IEC 60529 for solid and liquid ingress; and IEC 60721-4 for vibration reduction. Enclosing the adapter in enclosure 100, also adds extra protection to system 20, as is described below.

Figure 2A:
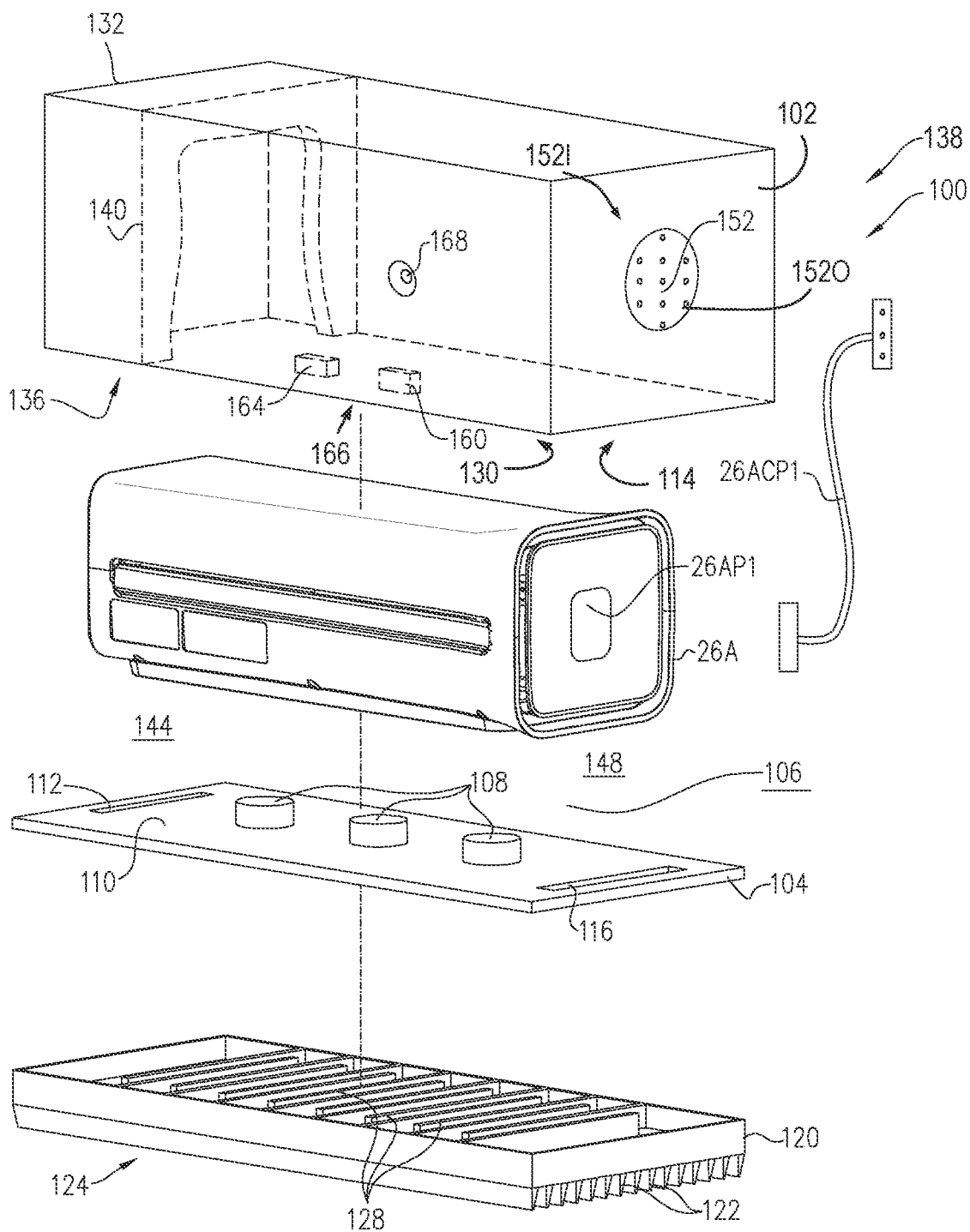
FIGS. 2A and 2B are schematic exploded diagrams of an enclosure and an adapter, according to an embodiment of the present invention.
Figure 2B:
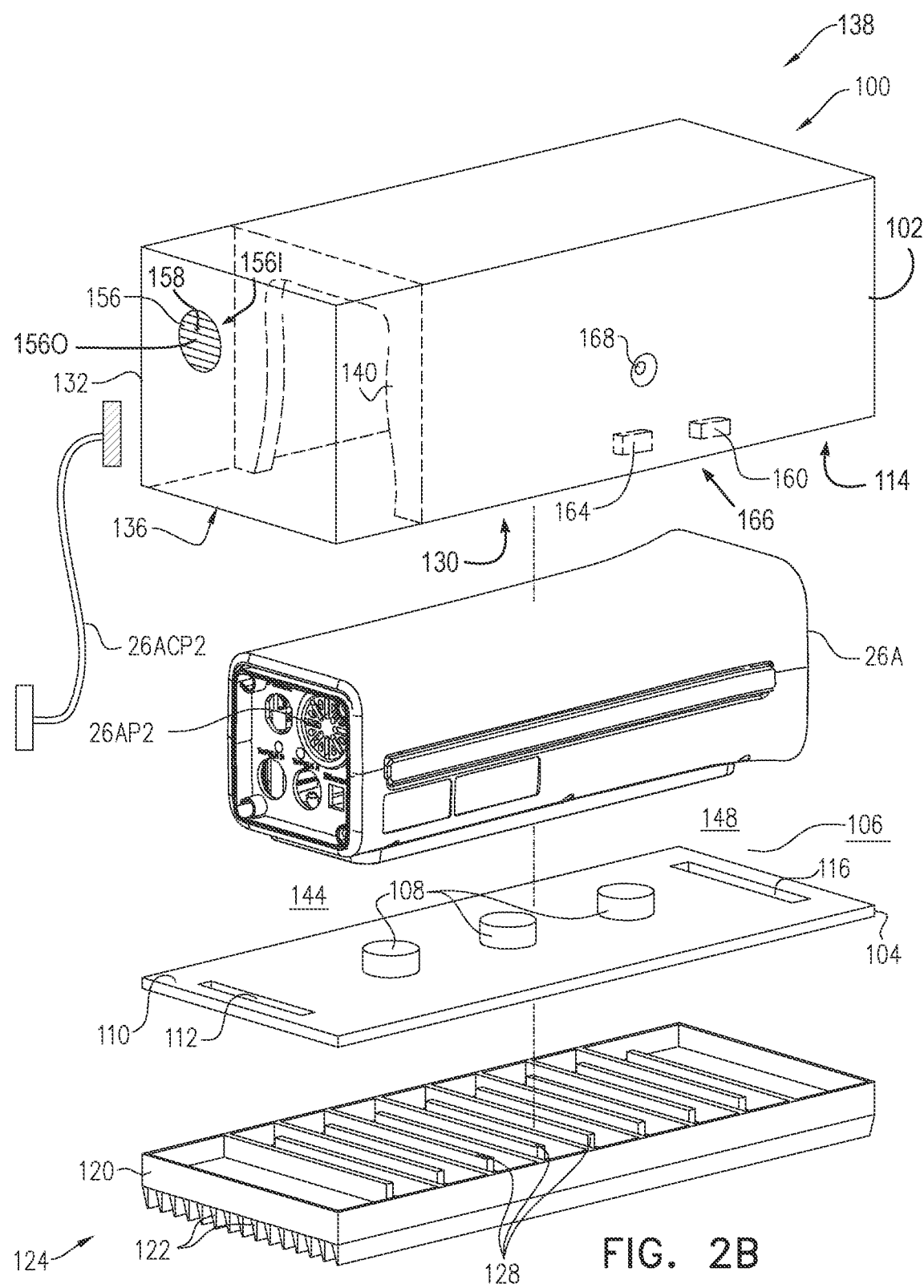

FIGS. 2A, 2B, are schematic exploded diagrams of enclosure 100 and adapter 26A, according to an embodiment of the present invention. The two figures show different sides of the enclosure. Enclosure 100 comprises a solid rectangular base 104, typically formed from an insulating plastic such as polyimide, which is coated on its upper surface with a conductive material, for example copper with a thickness of 1 mm. The conductive coating forms a conductive surface 110. On the base are cemented three substantially similar viscoelastic cylinders 108, which support adapter 26A, cemented to the cylinders, in a region 106 above the base. Cylinders 108 are configured to absorb vibrations to which base 104 is subjected. In one embodiment cylinders 108 are configured so that vibrations of 5-2000 Hz applied to the base do not affect the operation of adapter 26A when it is being supported by the base.

Base 104 comprises a first vent 112 and a second vent 116, and a closed heat dissipator 120 is attached to the base, so that it is beneath the base. Typically, a sealing gasket is located between base 104 and dissipator 120, to prevent ingress of water. Dissipator 120 comprises cooling fins 122 external to the dissipator, and a labyrinthine arrangement 124 of metal walls 128 within the dissipator. The walls are arranged so that hot air produced by adapter 120, when operative, in proximity to first vent 112, passes through the vent, and enters arrangement 124. The hot air travels through arrangement 124 and is cooled by fins 122 while it passes through, so that cooled air re-enters, via second vent 116, region 106.

A cover 132, typically in the form of an open rectangular parallelepiped or box, is configured to fit over and attach to base 104. Cover 132 is typically formed from an insulating plastic such as polyimide, and is coated on its inner surface with a conductive material, for example copper with a thickness of 1 mm, so forming an internal conductive surface 136. When cover 132 attaches to base 104, conductive surface 110 of the base contacts conductive surface 136 of the cover to form a shield 138, so that region 106 is effectively within a Faraday cage since it is substantially completely surrounded by conductive material.

The Faraday cage formed by connecting the two conductive surfaces attenuates magnetic fields alternating in a range of 10 kHz-100 kHz, and originating from outside the enclosure, by at least 20 dB.

Within cover 132 there is a dividing arch 140 which separates region 106 into two sub-regions. A first sub-region 144 is where the hot air described above, and produced by adapter 26A, is generated. A second sub-region 148 is where the cooled air from vent 116 returns.

A first connector 152 passes through an outer surface 102 and an inner surface 114 of enclosure 100, by being formed in a first side of cover 132, and a second connector 156 passes through the inner and outer surfaces of the enclosure by being formed in a second cover side opposite the first side. Each connector comprises multiple sets of feed-through pins passing between inner and outer sides of the connectors. Thus connector 152 has pins passing between an inner side 152I and an outer side 152O of the connector; and connector 156 has pins passing between an inner side 156I and an outer side 156O of the connector. Within region 106 a first port 26AP1 of adapter 26A is coupled by a first connecting cable 26ACP1 to connector 152. Also within region 106 a second port 26AP2 of adapter 26A is coupled by a second connecting cable 26ACP2 to connector 156.

When cover 132 attaches to base 104, the two conducting surfaces connect together, so as to form a Faraday cage around adapter 26A, as described above. While the Faraday cage acts as shield 138 to protect adapter 26A from external EM radiation, it will be understood that it is not completely impervious to such radiation. Consequently, there is typically leakage EM radiation within the Faraday cage that may compromise the operation of adapter 26A. Embodiments of the invention address this problem by providing further elements within enclosure 100, as described below.

An inside surface 130 of cover 132 is part of inside surface 114 of enclosure 100. Mounted on inside surface 130 of the cover is a magnetic radiation sensing circuit 160 comprising at least one coil. Circuit 160 is assumed herein to comprise a triple axis sensor (TAS) which has three orthogonal coils, and the circuit is also referred to herein as TAS 160. Also mounted on the inside surface of the cover is circuitry 164 comprising a lock-in amplifier. Circuitry 164 is coupled to receive a signal generated by sensing circuit 160. Circuit 160 and circuitry 164 together comprise a sensing circuit 166, and the sensing circuit senses a magnetic field within enclosure 100, and in response outputs a resultant signal.

Circuitry 164 receives power from connector 156, and is also coupled to receive a reference frequency, also herein termed a control signal. Herein, by way of example, the control frequency is assumed to be received from a pin 158 of connector 156 when the connector is coupled to interface 64 of console 40 (FIG. 1). Pin 158 acts as a control input for sensing circuit 166. However, it will be understood that there may be other forms for the control input, for example by having a conductor such as a feed-through conductor separate from connector 156 penetrating enclosure 100, or even by having a dial that provides the control signal mounted on the enclosure.

In a disclosed embodiment of the present invention, the reference frequency is one of the frequencies used by tracking module 60 to power field generators 62. Typically, tracking module 60 powers generators 62 simultaneously at different frequencies. In one embodiment circuitry 164 comprises a microcontroller which performs a fast Fourier transform (FFT) on incoming signals so as to select the reference frequency. Alternatively circuitry 164 is multiplexed to operate with all of the different frequencies of the tracking module.

Using the reference frequency, circuitry 164 measures the level of the sensing circuit signal at the reference frequency. If the measured level is greater than a preset value, indicating that the magnetic field traversing sensing circuit 160 is greater than a preset magnetic field threshold, then circuitry 164 is configured to generate a warning signal. In one embodiment the preset value of the sensing circuit signal is set at 1 μV, and this value is generated when the preset magnetic field threshold has an amplitude 1 mGauss.

The warning signal may be used to operate a warning light emitting element, such as a light emitting diode (LED) 168 mounted on cover 132. Alternatively or additionally, the warning signal may be provided to processor 32, via connector 156, and the processor may use the signal for other actions, such as providing a notification to operator 22 on screen 44 of the presence of the predefined magnetic field at adapter 26A, and/or recording that signals acquired by probe 26 have been acquired while the predefined magnetic field is present.

Typically, on being notified of the presence of the predefined magnetic field at adapter 26A, for instance by LED 168 illuminating, operator 22 may move enclosure 100 until the LED no longer illuminates, or until notified that the predefined magnetic field is no longer at the adapter.

FIG. 3A is a schematic block diagram illustrating probe 26, adapter 26A in enclosure 100, and console 40, and their matching connections, according to an embodiment of the present invention. As will be appreciated from the description above, as well as by inspection of FIG. 3A, probe 26 may connect directly to interface 64 since the connections of cable 26C and interface 64 match. Similarly, probe 26 may connect directly to port 26AP1 of adapter 26A, and port 26AP2 of the adapter may connect directly to interface 64, since the respective connections match.

Furthermore, as described herein, in embodiments of the present invention, when adapter 26A is in enclosure 100, probe 26 may connect to port 26AP1 of adapter 26A via connector 152 of the enclosure and associated cables/adapters of connector 152, and port 26AP2 of the adapter may connect to interface 64 via connector 156 and associated cables of connector 156, since all the respective connections match.

It will be appreciated that any given adapter 26A has specific functionalities that are applied to probe 26, and that other given adapters typically have different functionalities added to the probe, so that all such different functionalities are assumed to be comprised within the scope of the present invention.

FIG. 3B is a schematic block diagram illustrating a probe 126, an adapter 126A in enclosure 100, and console 40, and their matching connections, according to an alternative embodiment of the present invention. While the description above has assumed, for simplicity and clarity, a probe 26 having flexible distal end with multiple electrodes, with an associated adapter 26A housed in enclosure 100, it will be appreciated that the scope of the present invention comprises adapters, housed in enclosure 100, that are operative for other probes.

The figure illustrates a probe 126, which may be any electrophysiological probe known in the art, such as a basket catheter, a balloon catheter, or a focal catheter. An adapter 126A adds functionality to probe 126 when the adapter is housed in enclosure 100 and connected to console 40, and the connections between probe 126 and console 40 respectively correspond to those between probe 26 and the console, and operate substantially as described above with respect to probe 26.

Thus, cabling 126C is connected, via a cable adapter 126C2, to connector 152 in enclosure 100, and cabling 126C3 is connected between connector 156 in the enclosure and interface 64 of the console. Within enclosure 100 a first port 126AP1 of adapter 126A is coupled by a first connecting cable 126ACP1 to connector 152. Also a second port 126AP2 of adapter 126A is coupled by a second connecting cable 126ACP2 to connector 156.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. An apparatus, comprising:
an adapter circuit configured to process electrophysiological signals and generate an output signal in response thereto;
an enclosure, comprising:
  a base comprising a base conductive layer; and
  a cover, which comprises a cover conductive layer and is configured to mate with the base so that the base conductive layer connects to the cover conductive layer so as to form a shield configured to surround the adapter circuit and that attenuates electromagnetic radiation originating outside the enclosure in a frequency range of 10 kHz-100 kHz by at least 20 dB within the enclosure;
a first connector passing through an outer surface of the enclosure and having a first outer side configured to connect to a medical probe so as to receive the electrophysiological signals therefrom and a first inner side connected to convey the electrophysiological signals to the adapter circuit;

a second connector passing through the outer surface of the enclosure and having a second inner side connected to receive the output signal from the adapter circuit and a second outer side configured to connect to a console so as to convey the output signal thereto;

a control input, configured to receive a control signal indicative of a selection of a frequency within the range; and a sensing circuit, configured to sense a magnetic field within the enclosure and to output a warning signal to provide a notification to a user when the magnetic field at the frequency indicated by the control signal exceeds a preset threshold.

2. The apparatus according to claim 1, and comprising a plurality of viscoelastic mounts configured to support the adapter circuit on the base and to attenuate, at the adapter circuit, mechanical vibrations received by the base.

3. The apparatus according to claim 1, wherein the cover mates with a first side of the base, the apparatus further comprising a closed heat dissipator connected to a second side of the base opposite to the first side, the base further comprising vents configured to transfer hot air from a region in proximity to the adapter circuit through the heat dissipator so as to cool the hot air and return cooled air to the region.

4. The apparatus according to claim 1, and comprising a light emitting element formed on the cover, the element being configured to activate in response to generation of the warning signal.

5. The apparatus according to claim 1, wherein the sensing circuit comprises at least one coil coupled to provide an input signal to a lock-in amplifier.

6. The apparatus according to claim 5, wherein the medical probe is located in a magnetic field alternating at a preset frequency, and wherein the control signal is indicative of the preset frequency, and is provided to the lock-in amplifier.

7. The apparatus according to claim 6, wherein the preset frequency is generated by the console, and wherein the lock-in amplifier receives the control signal from the console via the second connector.

8. The apparatus according to claim 1, wherein the preset threshold comprises a magnetic field having an amplitude of 1 mGauss.

9. A method, comprising:

providing an adapter circuit configured to process electrophysiological signals and generate an output signal in response thereto;

providing an enclosure, comprising:

a base comprising a base conductive layer, and a cover, which comprises a cover conductive layer and is configured to mate with the base so that the base conductive layer connects to the cover conductive layer so as to form a shield configured to surround the adapter circuit and that attenuates electromagnetic radiation originating outside the enclosure in a frequency range of 10 kHz-100 kHz by at least 20 dB within the enclosure;

positioning the adapter circuit within the enclosure,;

passing a first connector through an outer surface of the enclosure, the first connector having a first outer side configured to connect to a medical probe so as to receive the electrophysiological signals therefrom and a first inner side connected to convey the electrophysiological signals to the adapter circuit;

passing a second connector through the outer surface of the enclosure, the second connector having a second inner side connected to receive the output signal from the adapter circuit and a second outer side configured to connect to a console so as to convey the output signal thereto;

configuring a control input to receive a control signal indicative of a selection of a frequency within the range; and configuring a sensing circuit to sense a magnetic field within the enclosure and to output a warning signal to provide a notification to a user when the magnetic field at the frequency indicated by the control signal exceeds a preset threshold.

10. The method according to claim 9, and comprising attaching a plurality of viscoelastic mounts to the base, the mounts being configured to support the adapter circuit on the base and to attenuate, at the adapter circuit, mechanical vibrations received by the base.

11. The method according to claim 9, wherein the cover mates with a first side of the base, the method further comprising connecting a closed heat dissipator to a second side of the base opposite to the first side, the base further comprising vents configured to transfer hot air from a region in proximity to the adapter circuit through the heat dissipator so as to cool the hot air and return cooled air to the region.

12. The method according to claim 9, and comprising forming a light emitting element on the cover, the element being configured to activate in response to generation of the warning signal.

13. The method according to claim 9, wherein the sensing circuit comprises at least one coil coupled to provide an input signal to a lock-in amplifier.

14. The method according to claim 13, wherein the medical probe is located in a magnetic field alternating at a preset frequency, and wherein the control signal is indicative of the preset frequency and is provided to the lock-in amplifier.

15. The method according to claim 14, wherein the preset frequency is generated by the console, and wherein the lock-in amplifier receives the control signal from the console via the second connector.

16. The method according to claim 9, wherein the preset threshold comprises a magnetic field having an amplitude of 1 mGauss.

* * * * *